US011690339B2

(12) United States Patent
Jeuken et al.

(10) Patent No.: US 11,690,339 B2
(45) Date of Patent: *Jul. 4, 2023

(54) ***BREMIA LACTUCAE* RESISTANT PLANTS**

(71) Applicants: RIJK ZWAAN ZAADTEELT EN ZAADHANDEL B.V., De Lier (NL); NUNHEMS B.V., Haelen (NL); VILMORIN & CIE, Paris (FR)

(72) Inventors: Marie Jeanette Willemijn Jeuken, De Lier (NL); Erik Den Boer, De Lier (NL); Richard Gerardus Franciscus Visser, De Lier (NL); Rients Engelhard Niks, De Lier (NL)

(73) Assignees: RIJK ZWAAN ZAADTEELT EN ZAADHANDEL B.V., De Lier (NL); NUNHEMS B.V., Haelen (NL); VILMORIN & CIE, Paris (FR)

( * ) Notice: Subject to any disclaimer, the term of this patent is extended or adjusted under 35 U.S.C. 154(b) by 105 days.

This patent is subject to a terminal disclaimer.

(21) Appl. No.: 16/571,370

(22) Filed: Sep. 16, 2019

(65) Prior Publication Data
US 2020/0000054 A1 Jan. 2, 2020

Related U.S. Application Data

(63) Continuation of application No. 15/262,071, filed on Sep. 12, 2016, now Pat. No. 10,440,914, which is a continuation-in-part of application No. PCT/EP2015/055322, filed on Mar. 13, 2015.

(30) Foreign Application Priority Data

Mar. 14, 2014 (EP) .................................... 14160096

(51) Int. Cl.
*A01H 6/14* (2018.01)
*A01H 1/04* (2006.01)
*A01H 1/00* (2006.01)
*A01H 1/02* (2006.01)
*A01H 5/12* (2018.01)
*C12Q 1/6895* (2018.01)

(52) U.S. Cl.
CPC ............ *A01H 6/1472* (2018.05); *A01H 1/021* (2021.01); *A01H 1/04* (2013.01); *A01H 1/045* (2021.01); *A01H 1/1255* (2021.01); *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,124,833 B2 | 2/2012 | Koorevaar et al. | |
| 9,006,521 B2 | 4/2015 | Zonneveld et al. | |
| 9,072,271 B2 | 7/2015 | Koorevaar et al. | |
| 10,440,914 B2 * | 10/2019 | Jeuken ................. | C12Q 1/6895 |
| 2099/0229010 | 9/2009 | Koorevaar et al. | |
| 2012/0117633 A1 | 5/2012 | Zonneveld et al. | |
| 2012/0204290 A1 | 8/2012 | Koorevaar et al. | |

FOREIGN PATENT DOCUMENTS

| | | |
|---|---|---|
| EP | 0 629 343 | 12/1994 |
| WO | 2009/111627 | 9/2009 |
| WO | 2011/003783 | 1/2011 |

OTHER PUBLICATIONS

CGN Germplasm (Centre for Genetic Resources L. saligna, The Netherlands; see https://cgngenis.wur.nl/ToonResultaten.aspx?ID=yab23vr2[May 9, 2018 4:05:22 PM]).*
Truco et al, 2013, Gene, Genomes, Genetics 3:617-631.*
Reyes-Chin-Wo et al, 2017, Nat. Commun. 8:14953, doi: 10.1038/ncomms14953.*
Centre for Genetic Resources CGN 15705 (1991, https://cgngenis.wur.nl/AccesionDetails.aspx?ID=hxwi445s&acnumber=CGN15705).*
Stassen et al (2013, MPMI 26:1259-1270).*
UCDavis map of LG9 (http:// https://cgpdb.ucdavis.edu/database/genome_viewer/_matrix_images/LM_JUN2005-JMR1-LG_9.x.large.png, accessed Jul. 21, 2021).*
Centre for Genetic Resources CGN 15705 (1991, https://cgngenis.wur.nl/AccessionDetails.aspx?ID=hxwi445s&acnumber=CGN15705, accessed May 3, 2018) (Year: 1991).
LG9 (http://cgpdb.ucdavis.edu/ GeneticMapViewer/_matrix_images/MJT-Map-DA0F-LG_9.x.large.png (Year: 2018).
CGN L saligna. The Netherlands; see https://cgngenis.wur.nl/ToonResultaten.aspx?1D=yab23vr2[May 9, 2018 4:05:22 PM] (Year: 2018).
Bonnier, et al., New sources of major gene resistance in Lactuca to Bremia lactucae, Euphytica (Jan. 1992) 61:203-211.
den Boer, et al., Fine mapping quantitative resistances to downy mildew in lettuce revealed multiple sub-QTLs with plant stage dependent effects reducing or even promoting the infection. Theoretical and Applied Genetics (Dec. 2013) 126(12):2995-3001.
Jeuken, et al., Efficient QTL detection for nonhost resistance in wild lettuce: backcross inbred lines versus F2 population, Theoretical and Applied Genetics (Feb. 2008) 116(6):845-857.

(Continued)

*Primary Examiner* — Anne Kubelik
(74) *Attorney, Agent, or Firm* — Duane Morris LLP; Thomas J. Kowalski; Deborah L. Lu

(57) ABSTRACT

The invention relates to a lettuce plant (*Lactuca sativa* L.) which may comprise a resistance allele which confers a broad spectrum resistance to *Bremia lactucae*, wherein the resistance allele is located on linkage group 9, and which resistance allele is as found in the genome of plants grown from seeds of which a representative sample was deposited under accession number NCIMB 42141. The invention further provides seeds, progeny, propagation material and food products from the plant.

12 Claims, 2 Drawing Sheets

Specification includes a Sequence Listing.

(56) References Cited

OTHER PUBLICATIONS

Jeuken, et al., Lactuca saligna, a non-host for lettuce downy mildew (*Bremia lactucae*), harbors a new race-specific Dm gene and three QTLs for resistance, Theoretical and Applied Genetics (Aug. 2002) 105(2-3):384-391.

Truco, et al., A high-density, integrated genetic linkage map of lettuce (*Lactuca* spp.) Theoretical and Applied Genetics (Sep. 2007) 115(6):735-746.

Zhang, et al., Three Combined Quantitative Trait Loci from Nonhost Lactuca saligna are Sufficient to Provide Complete Resistance of Lettuce Against Bremia lactucae, Molecular Plant-Microbe Interactions (Sep. 2009) 22-9:1160-1168.

International Search Report and Written Opinion of the International Searching Authority dated Jun. 24, 2015, issued in International Application No. PCT/EP2015/055322.

\* cited by examiner

BREMIA LACTUCAE RESISTANT PLANTS

RELATED APPLICATIONS AND INCORPORATION BY REFERENCE

This application is a continuation of U.S. application Ser. No. 15/262,071 filed Sep. 12, 2016, now allowed, which is a continuation-in-part application of International Patent Application Serial No. PCT/EP2015/055322 filed Mar. 13, 2015, which published as PCT Publication No. WO 2015/136085 on Sep. 17, 2015, which claims benefit of European Patent Application Serial No. EP 14160096.5 filed Mar. 14, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Sep. 9, 2016, is named Y795402001.txt and is 3,984 bytes in size.

FIELD OF THE INVENTION

The present invention relates to plants and plant parts, in particular lettuce plants (*Lactuca sativa* L.), which have a broad spectrum resistance to *Bremia lactucae*. The invention further relates to parts of these plants, to seeds, to propagation material, to the progeny of these plants, and use of the plants as germplasm in breeding for broad spectrum resistance to *Bremia lactucae*.

BACKGROUND OF THE INVENTION

*Bremia lactucae*, an oomycete, is the causal organism of downy mildew in lettuce (*Lactuca sativa* L.), and constitutes a major problem for lettuce production in both glass house and open field conditions. *Bremia lactucae* is an obligate parasite capable of infecting a lettuce plant in any growth stage from seedling to mature plant.

Downy mildew causes pale, angular, yellow areas bounded by veins on the upper leaf surfaces. Spore formation appears on the lower leaf surface as a white cottony-like fungal growth soon after initial symptom development. The lesions eventually turn brown, and they may enlarge and coalesce. These symptoms typically occur first on the lower leaves of the lettuce, but under ideal conditions may move into the upper leaves of the head. When the oomycete progresses to this degree, the head cannot be harvested. Less severe damage requires the removal of more leaves than usual, especially when the lettuce reaches its final destination. As such, every year this disease leads to millions of dollars of lost lettuce crop throughout the world.

Breeding for lettuce resistant against *Bremia lactucae* has been based upon the identification and introgression of resistance genes (R-genes), known in lettuce as Dm genes. When R-gene products of a lettuce plant recognize specific *Bremia* avirulence (Avr) gene products in a gene-for-gene interaction, this triggers downstream response pathways in the host plant. The result is an incompatible reaction associated with a hypersensitive cell death response by the host plant, thus providing race-specific resistance against *Bremia lactucae*.

However, R-genes may be rendered ineffective soon after they are introduced due to the rapid genetic adaption of the pathogen. As new *Bremia lactucae* races or isolates emerge, their Avr genes have been altered in such a way that allows the pathogen to evade recognition by the host and overcome race-specific resistance. Recognition of the altered Avr genes by existing R-genes is thus lost, and infection by newly emergent *Bremia lactucae* races or isolates can successfully be established resulting in disease. Re-establishment of resistance in the plant can only occur however, if novel R-genes are introduced into the plant which are able to recognize other Avr genes. Thus, the continual co-evolution of the plant and the pathogen has led to a so-called arms race.

The aforementioned arms race between the plant and the pathogen is a continuous evolutionary struggle. For the lettuce plant, this means that the resistance provided by existing R-genes are broken. Thus breeders require novel resistance genes in order to keep producing resistant varieties.

One breeding technique used to slow down the rapid adaption by newly emerging *Bremia* races or isolates is to stack or pyramid different R-genes, in order to provide new combinations of R-genes. R-genes are grouped together in a limited number of locations on the lettuce genome, known as resistance clusters. In lettuce, major resistance clusters are known to be located on linkage group 1, linkage group 2, linkage group 4, and linkage group 8 (linkage groups are numbered according to the integrated genetic map of lettuce, Truco et. al. (2007) Theoretical and Applied Genetics, 115(6): 735-46). R-genes from the same cluster can segregate as alleles or tightly linked genes. Therefore, it is often impossible to stack R-genes from the same cluster because genes on the same cluster are in repulsion phase (e.g. allelic) with one another and inherit like alternative alleles of the same locus. By combining R-genes and alleles from different clusters, in coupling phase, more durable forms of resistance may be bred. Moreover, novel R-genes with the potential to be stacked with existing R-genes are an extremely valuable asset to the breeder since the breeder has new stacking possibilities at hand, thus slowing down the virulence of the pathogen.

Quantitative Trait Loci (QTLs) for *Bremia* resistance derived from *L. saligna* CGN5271 have also been described, such as rbq1, rbq2 and rbq3, located on chromosome 7, 1 and 9 respectively (Jeuken et al. 2008, Theor Appl Genet 116: 845-857 and Jeuken and Lindhout 2002, Theor Appl Genet 105: 384-391). The recessive QTL rbq3 is located on the upper half of chromosome 9.

Citation or identification of any document in this application is not an admission that such document is available as prior art to the present invention.

SUMMARY OF THE INVENTION

Given the significant advantages of having alternative sources of resistance than those already present in the state of the art, it is the object of the present invention to provide lettuce plants with a new R-gene having resistance against *Bremia lactucae*. Additionally, it is the object of the present invention to further increase the durability of (existing) resistance against *Bremia lactucae* by providing lettuce plants with an R-gene that is located outside of known resistance clusters.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with National Collections of Industrial, Food and Marine Bacteria (NCIMB), Ferguson Building, Craibstone Estate, Bucksburn, Aberdeen, AB21 9YA Scotland UK, under deposit accession number NCIMB 42141 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

Figure 2:
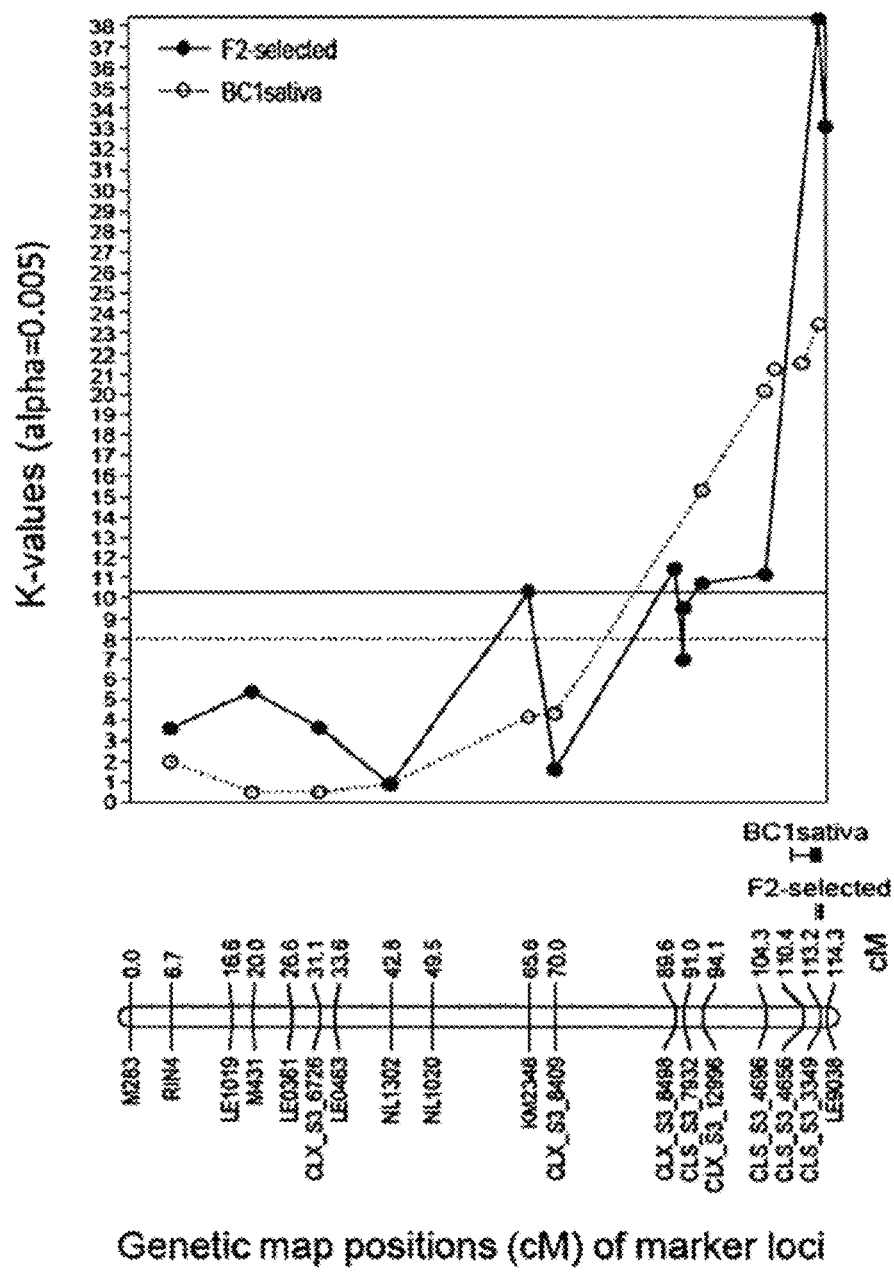

Column A, shows examples of six leaf discs that differ in the percentage of the leaf surface covered by sporangiophores of *Bremia lactucae*. Column B, shows the same six leaf discs which have been sectioned in order to facilitate counting of the sporangiophores. The estimated percentage of sporangiophores on the leaf disc surface is indicated.

FIG. 2: Association between marker loci and infection severity levels to *Bremia lactucae* at linkage group 9. Kruskal-Wallis test results (K values, alpha=0.005) are plotted indicating the significant peak values for the selected F2 population (solid lines) and the BC1sativa population (dashed lines). The bott_C9 resistance allele of both populations is identified by markers CLS_S3_3349 and/or CLS_S3_4656, and/or other linked markers which are less than 10 cM away from the resistance allele. The resistance allele is located on the lower or bottom portion of linkage group 9, below marker CLS_S3_7932, which is a marker also found on the integrated genetic map of lettuce.

DETAILED DESCRIPTION OF THE INVENTION

In the research that led to the present invention, novel lettuce plants (*Lactuca sativa* L.) were developed such that they are resistant against *Bremia lactucae*, and in particular, have a broad spectrum resistance against this pathogen.

The said resistance of the invention is controlled by a resistance allele on the bottom of linkage group 9, the inheritance of which is consistent with that of a monogenic dominant trait. The term "dominant" is to mean in this context that the fully achievable resistance is observable in plants which comprises the resistance allele in the homozygous or heterozygous state. The resistance allele according to the invention or an introgression fragment which comprises the resistance allele, is obtainable from the genome of a distantly related wild species, in particular from the genome of wild accessions of *Lactuca saligna* containing the bott_C9 resistance allele which confers broad spectrum *Bremia lactucae* resistance, including but not limited to, CGN 15705. While the resistance allele in the context of the invention is obtainable from e.g. *L. saligna* accession CGN 15705, it is not intended to preclude others to use this accession per se. Therefore, the invention relates only to the bott_C9 resistance allele when present in a *L. sativa* background.

The present invention thus relates to a cultivated lettuce plant which comprises a resistance allele which confers a broad spectrum resistance to *Bremia lactucae*, wherein the resistance allele is located on the bottom of linkage group 9. The resistance allele is located on an *L. saligna* fragment between markers CLS_S3_4656 and CLS_S3_3349 or is located below CLS_S3_3349 (SEQ ID NO:1), towards the end of the chromosome as shown in FIG. 2. Thus, in one embodiment a cultivated lettuce plant is provided which comprises an introgression from *L. saligna* on the bottom of chromosome 9, wherein the introgression comprises the sequence of SEQ ID NO: 1 (identifiable using primers of SEQ ID NO: 6 and 7) and/or SEQ ID NO:3 (identifiable using primers of SEQ ID NO: 8 and 9) and/or any *L. saligna*-genome specific marker in between markers CLS_S3_4656 and CLS_S3_3349 or is located below CLS_S3_3349 (SEQ ID NO:1), towards the end of the chromosome as shown in FIG. 2. In one aspect of the invention, the resistance allele is as found in plants grown from seeds of which a representative sample was deposited under accession number NCIMB 42141. In another aspect of the invention, the resistance allele is introgressed from another *Lactuca saligna* accession containing the bott_C9 resistance allele which confers broad spectrum *Bremia lactucae* resistance. Such a *Lactuca saligna* accession may be identified using one or more molecular markers linked to the bott_C9 resistance allele, for example by one or more of the markers defined herein, such as the markers of SEQ ID NO:1 (marker CLS_S3_3349) and/or SEQ ID NO:3 (marker CLS_S3_4656) and/or any marker in between markers CLS_S3_4656 and CLS_S3_3349 or is located below CLS_S3_3349 (SEQ ID NO:1), towards the end of the chromosome as shown in FIG. 2, or any other marker linked to the resistance allele. Subsequently, those *L. saligna* accessions having been identified using one or more molecular markers linked to the bott_C9 resistance allele and which comprises the resistance allele of the invention, may be confirmed by phenotypically screening the progeny of a cross between the *L. saligna* accession and a cultivated lettuce plant for broad spectrum *Bremia lactucae* resistance. Thus, other *L. saligna* plants which comprises the resistance allele on the bottom of chromosome 9 can be identified by e.g. screening *L. saligna* plants for the presence of markers of SEQ ID NO: 1 and/or SEQ ID NO:3 and/or any *L. saligna* marker in between markers CLS_S3_4656 and CLS_S3_3349 or is located below CLS_S3_3349 (SEQ ID NO:1), towards the end of the chromosome as shown in FIG. 2, and/or for other markers linked to the bott_C9 allele, followed by crossing with a cultivated lettuce plant and phenotypically screening the progeny for broad spectrum *Bremia lactucae* resistance. Other *L. saligna* markers linked to the bott_C9 allele can be developed by e.g. sequencing the bott_C9 region or by analyzing a segregating population from a cross between a resistant plant and a susceptible plant and identifying other molecular markers that co-segregate with the resistance phenotype.

In one embodiment, the broad spectrum resistance allele on the bottom of linkage group 9 is linked to markers CLS_S3_3349 (SEQ ID NO:1) and/or marker CLS_S3_4656 (SEQ ID NO:3). Thus, in one embodiment the cultivated lettuce plant may comprise an introgression fragment from an *L. saligna* plant on the bottom of chromosome 9, wherein said *L. saligna* introgression fragment may comprise the sequence of SEQ ID NO: 1 (identifiable using primers of SEQ ID NO: 6 and 7) and/or SEQ ID NO:3 (identifiable using primers of SEQ ID NO: 8 and 9) and/or any *L. saligna*-genome specific marker (physically located) in between markers CLS_S3_4656 and CLS_S3_3349 or is located below CLS_S3_3349 (SEQ ID NO:1), towards the end of the chromosome as shown in FIG. 2. In one aspect the introgression fragment may comprise the sequence of SEQ ID NO: 1 through to the sequence of SEQ ID NO: 3, i.e. also the *L. saligna* nucleic acid sequence in between SEQ ID NO:1 and SEQ ID NO:3. In another aspect the introgression fragment may comprise a resistance-conferring fragment of the *L. saligna* sequence ranging from marker CLS_S3_4656 to marker CLS_S3_3349. The fragment may comprise only one of these two markers or it may lack both markers, as long as it retains the resistance conferring *L. saligna* sequence molecule.

In a specific embodiment, the presence of the broad spectrum resistance allele on the bottom of linkage group 9 is detectable by markers CLS_S3_3349 (SEQ ID NO:1) and/or marker CLS_S3_4656 (SEQ ID NO:3).

Thus, when referring herein to a plant or plant part which comprises a broad spectrum resistance allele from *Lactuca saligna* obtainable from NCIMB 42141, the embodiments also comprises a broad spectrum *Bremia* resistance allele on the bottom of linkage group 9 obtainable from CGN 15705 or from other *Lactuca saligna* accessions containing the bott_C9 resistance allele which confers broad spectrum *Bremia lactucae* resistance and wherein the genomic DNA comprises an introgression fragment on the bottom of chromosome 9 which comprises the sequence of SEQ ID NO: 1 and/or SEQ ID NO:3 and/or any *L. saligna*-genome specific marker in between markers CLS_S3_4656 and CLS_S3_3349 or is located below CLS_S3_3349 (SEQ ID NO:1), towards the end of the chromosome as shown in FIG. 2.

In one embodiment, broad spectrum resistance conferred by the resistance allele on the bottom of linkage group 9 is to at least the following *Bremia lactucae* isolates: B1:10, B1:15, B1:16, B1:21, B1:24, B1:25, B1:26, B1:27, and B1:28.

In a further embodiment, broad spectrum resistance conferred by the resistance allele on the bottom of linkage group 9 is to at least the following *Bremia lactucae* isolates: B1:10, B1:15, B1:21, B1:25, B1:26, B1:27 and B1:28.

In another embodiment, broad spectrum resistance conferred by the resistance allele on the bottom of linkage group 9 is to at least the following *Bremia lactucae* isolates: B1:10, B1:24, B1:25, B1:26, and B1:28.

Furthermore, it was found during the research leading to the present invention that the resistance allele conferring a broad spectrum resistance to *Bremia lactucae* is located on the bottom of linkage group 9, below marker CLS_S3_7932, and is linked to markers CLS_S3_3349 (SEQ ID NO:1) and/or CLS_S3_4656 (SQ ID NO:3) (Table 1) and is located in between these two markers. It is noted that the quantitative resistance gene rbq3 is located on the upper half of linkage group 9, above marker CLS_S3_4656 and also above marker KM2348 (FIG. 2), said marker KM2348 being described in Jeuken et al. 2008 (supra).

More in particular, in the deposit NCIMB 42141 the resistance allele conferring a broad spectrum resistance to *Bremia lactucae* is located on the bottom of linkage group 9 of the integrated genetic linkage map of lettuce, below marker CLS_S3_7932, linked to markers CLS_S3_3349 (SEQ ID NO:1) and/or CLS_S3_4656 (SEQ ID NO:3) (Table 1).

The said resistance allele on the bottom of linkage group 9 is advantageous to a breeder since it may be stacked with existing R-genes on other resistance clusters, for example Dm1, Dm2, Dm4, Dm5/8, Dm 6, Dm7, Dm10, Dm12, Dm13, Dm14, Dm15, Dm17, Dm18, R36, R37 or R38, or any combinations thereof. Likewise it may also be stacked with quantitative resistance genes, such as rbq1, rbq2 and/or rbq3. This enables the breeder to create new combinations of resistance against *Bremia lactucae*, thereby slowing down the virulence of the pathogen.

The invention also relates to a cultivated lettuce plant having a broad spectrum resistance to *Bremia lactucae*, which comprises a resistance allele that confers a broad spectrum resistance to *Bremia lactucae*, wherein said resistance allele is obtainable by, or obtained by, crossing a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, such as found in a plant grown from seeds of which a representative sample was deposited under accession number NCIMB 42141, with another lettuce plant, and wherein said resistance allele is as in the seeds of *Lactuca saligna* accessions containing the bott_C9 resistance allele which confers broad spectrum *Bremia lactucae* resistance, in particular in the seeds of the seed deposit number NCIMB 42141, is positioned on linkage group 9 and linked to one or more markers within 10 cM or less from the resistance allele, such as any marker below marker CLS_S3_7932, such as marker CLS_S3_3349 (SEQ ID NO:1) and/or CLS_S3_4656 (SEQ ID NO:3) and/or any marker in between markers CLS_S3_3349 (SEQ ID NO:1) and CLS_S3_4656 (SEQ ID NO:3).

In one aspect the lettuce plant is a cultivated lettuce plant and may comprise in its genome an introgression fragment from *L. saligna*, wherein said introgression fragment may comprise at least one sequence selected from the group consisting of: CLS_S3_3349 (SEQ ID NO:1), CLS_S3_4656 (SEQ ID NO:3), any *L. saligna* genome specific sequence in between SEQ ID NO:1 and SEQ ID NO:3, a *L. saligna* genome specific marker linked to CLS_S3_3349 (SEQ ID NO:1) or CLS_S3_4656 (SEQ ID NO:3) within 10 cM or less, and whereby the introgression fragment confers broad spectrum resistance to *Bremia lactucae* onto said cultivated lettuce plant.

In one embodiment, the invention provides a cultivated lettuce plant that is resistant against *Bremia lactucae*, obtainable by crossing a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, in particular as found in the genome of seeds of which representative seed was deposited under accession number NCIMB 42141, with another lettuce plant to produce an F1, optionally selfing said F1 one or more times to obtain an F2 or further selfing progeny and/or backcrossing the F1, F2, or further selfing progeny to another lettuce plant, and selecting a plant that shows broad spectrum resistance to *Bremia lactucae*.

In a still further embodiment, the invention relates to a lettuce plant, which has a broad spectrum resistance to *Bremia lactucae*, and which plant is obtainable by crossing a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, in particular as found in a lettuce plant grown from seeds of which a representative sample was deposited under accession number NCIMB 42141, and selecting in the F2, F3, etc. or BC1, BC2 etc. progeny of the cross that is obtained after crossing the F1 with itself or with another plant, for plants showing a broad spectrum resistance to *Bremia lactucae* and/or for one or more markers selected from the group: CLS_S3_3349 (SEQ ID NO:1), CLS_S3_4656 (SEQ ID NO:3), any *L. saligna* genome specific sequence in between SEQ ID NO:1 and SEQ ID NO:3, any *L saligna* genome specific marker linked to CLS_S3_3349 (SEQ ID NO:1) or CLS_S3_4656 (SEQ ID NO:3) within 10 cM or less.

A lettuce plant carrying the resistance allele conferring a broad spectrum resistance to *Bremia lactucae* can be suitably identified amongst descendants from a cross between a plant susceptible to *Bremia lactucae*, and a plant that carries the resistance allele of the invention to produce an F1, optionally selfing said F1 one or more times to obtain an F2, F3 or further selfing progeny or BC1, BC2 or further backcross progeny, and selecting plants showing the broad spectrum *Bremia* resistance trait. Plants can be identified and/or selected on the basis of determining the phenotype through an Adult Plant Disease Test, and/or through the identification of the resistance allele, for example by means of one or more of the markers defined herein.

An Adult Plant Disease Test, as used herein, is a *Bremia* disease testing method used to discern between plants that are susceptible or resistant against various strains or isolates of *Bremia lactucae*. To perform an Adult Plant Disease Test, leaf discs of 8 week old plants (e.g. 6-8 leaf stage) are used, and which plants have not started to bolt. This is done to ensure that bolting does not have an influence on resistance scoring. For each *Bremia lactucae* strain to be tested, 3 or 4 leaf discs per plant are sampled, and more in particular, each of the leaf discs are sampled from different leaves of the plant. In one aspect of the invention, leaf disc samples are taken from the top leaves, the middle leaves, and the bottom leaves of the plant.

Leaf discs are placed upside down on wetted filter paper, inside a plastic box. Subsequently, the leaf discs are inoculated by spraying with a spore suspension of the *Bremia lactucae* strain to be tested, such as at a spore concentration of approximately $10^4$-$10^5$ spores per ml. Leaf discs of resistant and susceptible controls are also included in the test.

Following inoculation, leaf discs are placed in a climate cell and incubated in the dark, in particular for at least 12-16 hours. The filter paper is kept moist with water to ensure that the humidity in the box remains, in particular between 95-100% humidity. In one aspect, the box containing the leaf discs are then transferred to a climate cell with the following conditions: photoactive period of 12 hours, constant temperature of 15° C., and light conditions of 20 W/m$^2$.

Scoring of the leaf discs takes place in particular at 8, 10 and 13 days post-inoculation. Each leaf disc is scored based upon the percentage of sporulation on the leaf disc surface (e.g. 0% to 100% sporulation). In one aspect of the invention, scoring is performed by a single person in order to prevent scoring biases.

In the absence of molecular markers or in the event that recombination between the molecular markers and the resistance allele have taken place and these are not predictive anymore, equivalence of resistance alleles can still be determined by an allelism test. To perform an allelism test, material that is homozygous for the known determinant (e.g. NCIMB 42141), the so-called tester plant, is crossed with material that is homozygous for the resistance allele that is to be tested. This latter plant is referred to as the donor plant. The donor plant to be tested should be or should be made homozygous for the resistance allele to be tested. The skilled person is aware of how to obtain a plant that is homozygous for the resistance allele to be tested. When in the F2 of the cross between a donor plant and a tester plant, no segregation for the phenotype related to the resistance allele is observed, the resistance allele of the donor plant and the tester plant have been proven to be equivalent or the same.

The invention also relates to a lettuce plant that comprises a resistance allele conferring a broad spectrum resistance to *Bremia lactucae*, wherein plants of the first generation progeny (F1) of a cross of the said plant with a tester plant that comprises the resistance allele as found in the genome of plants grown from seeds of which a representative sample was deposited under accession number NCIMB 42141, or a progeny plant thereof that comprises the said resistance allele, or a plant derived there from and which comprises the said resistance allele, show no segregation for broad spectrum resistance to *Bremia lactucae*. In both the tester plant and the plant of the invention, the resistance allele is present in homozygous form. Plants of the second and further generations, if obtained by selfing, will also show no segregation for the said resistance pattern. The tester plant can be a plant of which representative seed was deposited under accession number NCIMB 42141.

The cultivated lettuce plant of the invention can be any one of the types from the following group: iceberg or crisphead, butterhead, romaine or cos, green leaf, red leaf, lollo, oakleaf, curly, incised leaf, multileaf, cutting, stem, Batavia, and Latin lettuce.

In another embodiment, the invention relates to seeds which comprises the said resistance allele conferring a broad spectrum resistance to *Bremia lactucae*. A plant grown from the seeds has a broad spectrum resistance to *Bremia lactucae*. In one aspect of the invention, the resistance allele is the allele as present in the genome of plants grown from seeds of which a representative sample was deposited under accession number NCIMB 42141.

The invention further relates to seeds of the resistant plants. According to the invention, plants grown from such seeds also show the broad spectrum *Bremia lactucae* resistance.

The invention also relates to progeny of the plants, cells, tissues, and seeds of the invention. Such progeny can in itself be plants, cells, tissues, or seeds.

Thus in one embodiment, the invention relates to progeny of a lettuce plant which comprises the resistance allele of the invention.

In a further embodiment, the invention relates to progeny of lettuce plants of the invention having broad spectrum resistance to *Bremia lactucae* conferred by a resistance allele from *L. saligna* on the bottom of linkage group 9. These progeny plants thus comprises the resistance allele on the bottom of linkage group 9, introgressed from a wild *Lactuca saligna* accession containing the bott_C9 resistance allele which confers broad spectrum *Bremia lactucae* resistance. The presence of the introgression which comprises the resistance allele can be determined phenotypically, using for example the Adult Plant Disease Test as described herein, and/or using one or more molecular markers linked to the resistance allele, such as the markers of SEQ ID NO:1 and/or SEQ ID NO:3 and/or any *L. saligna* marker located physically in between SEQ ID NO: 1 and SEQ ID NO: 3, or any other marker(s) physically linked to the resistance allele on the bottom of linkage group 9. The resistance allele is in one embodiment the allele as present in the genome of plants grown from seeds of which a representative sample was deposited under accession number NCIMB 42141.

According to a further aspect thereof, the invention relates to propagation material capable of growing into a plant of the invention.

In one embodiment, such propagation material is formed by a seed of the lettuce plant of the invention, wherein the plant that can be grown from the seed comprises a resistance allele of the invention.

In a further embodiment, the propagation material capable of growing into a plant of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

In an additional embodiment, the invention relates to a tissue culture of propagation material capable of growing into a plant of the invention.

In another embodiment, the plant produced from the propagation material comprises the resistance allele as found in lettuce plants which may comprise a resistance allele on the bottom of linkage group 9, as found in the genome of seeds of *Lactuca saligna* accessions containing the bott_C9 resistance allele which confers broad spectrum *Bremia lactucae* resistance, in particular as found in lettuce plants grown from seeds of which a representative sample was deposited under accession number NCIMB 42141 or progeny or descendants of such plants which retain the *L. saligna* introgression.

The invention also relates to the harvested part of the lettuce plant which comprises the resistance allele conferring a broad spectrum resistance to *Bremia lactucae*.

Moreover, the invention relates to a food product which comprises one or more harvested parts of a lettuce plant, for example harvested leaves and/or heads, which comprises the resistance allele conferring a broad spectrum resistance to *Bremia lactucae*. The harvested part or food product can be, or may comprise the lettuce head and/or leaves of a lettuce plant or a salad mixture which may comprise leaves of the lettuce plant of the invention. The food product or harvested part may have undergone one or more processing steps. Such a processing step might comprise but is not limited to any one of the following treatments or combinations thereof: cutting, washing, mixing, etc. The processed form that is obtained is also part of this invention.

Another aspect of this invention relates to a nucleic acid molecule which is causative of broad spectrum resistance to *Bremia lactucae*. The said DNA molecule comprises a DNA sequence which is positioned on linkage group 9 and in particular linked to markers CLS_S3_3349 (SEQ ID NO:1) and/or CLS_S3_4656 (SEQ ID NO:3). The nucleic acid molecule is also part of this invention. In one embodiment, the nucleic acid molecule is the resistance allele, optionally in isolated form. The nucleic acid sequence may or may not comprise either or both markers. When the markers are not present but the nucleic acid still confers broad spectrum resistance to *Bremia lactucae*, the nucleic acid is still part of the invention. The nucleic acid molecule can be used in the production of *Bremia lactucae* resistant lettuce plants. In one aspect of the invention, the nucleic acid molecule comprises the resistance allele as present in the genome of plants grown from seeds of which a representative sample was deposited under accession number NCIMB 42141.

Yet another aspect of the invention relates to use of the markers and said nucleic acid molecule to identify plants which have a broad spectrum resistance to *Bremia lactucae*, and/or carrying the resistance allele conferring a broad spectrum resistance to *Bremia lactucae*.

Therefore in one embodiment the invention relates to the use of markers CLS_S3_3349 (SEQ ID NO:1) and/or CLS_S3_4656 (SEQ ID NO:3), or the said DNA molecule which may comprise a DNA sequence which is positioned on the bottom of linkage group 9 and is optionally linked to markers CLS_S3_3349 (SEQ ID NO:1) and/or CLS_S3_4656 (SEQ ID NO:3), or part thereof, to identify plants which have a broad spectrum resistance to *Bremia lactucae* and/or carry the resistance allele conferring a broad spectrum resistance to *Bremia lactucae*.

The skilled person knows how to develop new markers linked to a trait using already known markers, QTLs, alleles, genes or other DNA molecules that are associated with a certain trait.

Thus, the invention also relates to the use of markers CLS_S3_3349 (SEQ ID NO:1) and/or CLS_S3_4656 (SEQ ID NO:3), and the said DNA molecule, or part thereof, for developing other markers linked to the resistance allele conferring a broad spectrum resistance to *Bremia lactucae*.

Further, the invention relates to the use of markers CLS_S3_3349 (SEQ ID NO:1) and/or CLS_S3_4656 (SEQ ID NO:3), and the said DNA molecule, or part thereof, for transferring the broad spectrum resistance allele to other lettuce plants and/or for detecting the presence of the broad spectrum resistance allele on the bottom of linkage group 9 in lettuce plants, e.g. in progeny or descendants of plants of the invention, and/or for screening *L. saligna* accessions for the presence of a broad spectrum resistance allele on the bottom of linkage group 9. Such *L. saligna* accessions can then be used to introgress at least the resistance conferring part of the bottom of linkage group 9 into cultivated lettuce. Any *L. saligna* accession may be screened using the markers. The markers can then also be used to screen progeny of a cross between an *L. saligna* accession and a cultivated lettuce plant and to select those progeny which may comprise the markers and have broad spectrum resistance to *Bremia lactucae*.

In one aspect the invention relates to a process for producing lettuce plants which comprises a resistance allele that confers a broad spectrum resistance to *Bremia lactucae*, which may comprise the step of selecting said lettuce plants from a population of lettuce plants segregating for the said resistance allele using markers CLS_S3_3349 (SEQ ID NO:1, SEQ ID NO:2) and/or CLS_S3_4656 (SEQ ID NO:3, SEQ ID NO:4).

The invention further relates to a cell of a lettuce plant of the invention, which cell comprises in its genome a resistance allele which leads to a broad spectrum resistance to *Bremia lactucae*, wherein the said resistance allele is as present in the genome of a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, in particular as present in the genome of a lettuce plant, representative seeds of which were deposited under accession number NCIMB 42141. The said cell thus comprises in its genome the genetic information encoding the said broad spectrum resistance to *Bremia lactucae*, in particular genetic information which is substantially identical to a resistance allele on the bottom of linkage group 9, as found in the genome of seeds of *Lactuca saligna* accessions containing the bott_C9 resistance allele which confers broad spectrum *Bremia lactucae* resistance. In one embodiment the said genetic information is essentially completely identical to the genetic information encoding the said broad spectrum resistance to *Bremia lactucae*, as present in a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, in particular as present in a lettuce plant, representative seeds of which were deposited under accession number NCIMB 42141. The extent of identity of the genetic information is such that the function of the genetic information, i.e. conferring broad spectrum *Bremia lactucae* resistance, is maintained.

In one embodiment, the cell of the invention is part of a plant or plant part, but the cell may also be in isolated form.

The invention also relates to a cell of a lettuce plant of the invention, which cell comprises a resistance allele which leads to a broad spectrum resistance to *Bremia lactucae*, and which plant is obtainable by or obtained by transferring the said resistance, as found in a lettuce plant which comprises a resistance allele on the bottom of linkage group 9, as found in the genome of seeds of *Lactuca saligna* accessions containing the bott_C9 resistance allele which confers broad spectrum *Bremia lactucae* resistance, in particular as found in seeds of which a representative sample was deposited under accession number NCIMB 42141, into an agronomically valuable lettuce plant.

The invention further relates to seed of the lettuce plant of the invention, which seed contain in their genome the genetic information that encodes the broad spectrum resistance to *Bremia lactucae*, i.e. the resistance allele.

The invention also relates to the use of seeds of *Lactuca saligna* accessions or other plants which comprises the bott_C9 resistance allele which confers broad spectrum *Bremia lactucae* resistance, in particular the use of seeds of which a representative sample was deposited under accession number NCIMB 42141 for transferring the bott_C9 resistance allele which confers broad spectrum resistance to *Bremia lactucae* into another agronomically valuable lettuce plant.

The invention also relates to the use of a lettuce plant of the invention that exhibits a broad spectrum resistance to *Bremia lactucae* due to the presence, in the genome of the plant, of the said resistance allele as found in the genome of seeds of *Lactuca saligna* accessions containing the bott_C9 resistance allele which confers broad spectrum *Bremia lactucae* resistance, in particular as found in the genome of seeds of which a representative sample was deposited under accession number NCIMB 42141, as a crop.

The invention also relates to the use of a lettuce plant of the invention that exhibits a broad spectrum resistance to *Bremia lactucae* due to the presence, in the genome of the plant, of the said resistance allele as found in the genome of seeds of *Lactuca saligna* accessions containing the bott_C9 resistance allele which confers broad spectrum *Bremia lactucae* resistance, in particular as found in the genome of seeds of which a representative sample was deposited under accession number NCIMB 42141, as a source of seed.

The invention also relates to the use of a lettuce plant of the invention that exhibits a broad spectrum resistance to *Bremia lactucae* due to the presence, in the genome of the plant, of the said resistance allele as found in the genome of seeds of *Lactuca saligna* accessions containing the bott_C9 resistance allele which confers broad spectrum *Bremia lactucae* resistance, in particular as found in the genome of seeds of which a representative sample was deposited under accession number NCIMB 42141, as a source of propagating material.

The invention also relates to the use of a lettuce plant of the invention that exhibits a broad spectrum resistance to *Bremia lactucae* due to the presence, in the genome of the plant, of the said resistance allele as found in the genome of seeds of *Lactuca saligna* accessions containing the bott_C9 resistance allele which confers broad spectrum *Bremia lactucae* resistance, in particular as found in the genome of seeds of which a representative sample was deposited under accession number NCIMB 42141, for consumption.

The invention also relates to the use of a lettuce plant of the invention that exhibits a broad spectrum resistance to *Bremia lactucae* due to the presence, in the genome of the plant, of a resistance allele as found in the genome of seeds of *Lactuca saligna* accessions containing the bott_C9 resistance allele which confers broad spectrum *Bremia lactucae* resistance, in particular as found in the genome of seeds of which a representative sample was deposited under accession number NCIMB 42141, for conferring resistance to *Bremia lactucae* on a *Lactuca sativa* plant.

According to a further aspect thereof, the invention relates to the use of a *Lactuca sativa* plant as a recipient of a *Bremia lactucae* resistance allele as found in the genome of seeds of

*Lactuca saligna* accessions containing the bott_C9 resistance allele which confers broad spectrum *Bremia lactucae* resistance, in particular as found in the genome of seeds of which a representative sample was deposited under accession number NCIMB 42141.

In one aspect the invention relates to a method for producing a lettuce plant having a broad spectrum resistance to *Bremia lactucae*, which may comprise:
 a) crossing a plant which may comprise a resistance allele that leads to a broad spectrum resistance to *Bremia lactucae* with another lettuce plant;
 b) optionally selfing the resulting F1 one or more times for obtaining F2, F3 or further selfing progeny plants;
 c) selecting plants having a broad spectrum resistance to *Bremia lactucae*;
 d) optionally performing one or more additional rounds of selfing and/or crossing, and subsequently selecting for a plant which may comprise the trait Selection can be performed phenotypically and/or using molecular markers linked to the trait.

It is clear that the parent that provides the trait of the invention is not necessarily a plant grown directly from the deposited seeds. The parent can also be a progeny plant from the seed or a progeny plant from seeds that are identified to have the trait of the invention by other means; or a wild *Lactuca saligna* accession containing the bott_C9 resistance allele, as determined by the expression of a broad spectrum *Bremia lactucae* resistance phenotype and/or the presence of molecular markers linked to the said resistance allele; or a cultivated lettuce plant which may comprise such a *Lactuca saligna* introgression on the bottom of linkage group 9.

In one embodiment the invention relates to a method for producing a lettuce plant having a broad spectrum resistance to *Bremia lactucae*, which may comprise:
 a) crossing a plant which comprises a resistance allele that leads to a broad spectrum resistance to *Bremia lactucae* with another lettuce plant;
 b) optionally selfing the F1 one or more times to produce an F2, F3, or further selfing progeny;
 c) optionally backcrossing the resulting F1 (or F2, F3, etc.) with either parent to obtain a backcross progeny plant;
 d) selecting for plants that have a broad spectrum resistance to *Bremia lactucae* in the F1 or further selfing progeny or backcross progeny;
 e) optionally performing one or more additional rounds of selfing or crossing, and subsequently selecting for a plant showing said broad spectrum resistance to *Bremia lactucae* or which comprises said resistance allele.

The present invention additionally provides a method for introducing another desired trait into a lettuce plant showing a broad spectrum resistance to *Bremia lactucae*, which may comprise:
 a) crossing a lettuce plant showing a broad spectrum resistance to *Bremia lactucae*, representative seeds of which were deposited under accession number NCIMB 42141, with a second lettuce plant that may comprise a desired trait to produce F1 progeny and optionally selfing said F1 progeny one or more times to produce further selfing progeny;
 b) selecting an F1 or further selfing progeny that comprises said resistance allele or shows said broad spectrum resistance to *Bremia lactucae* and the desired trait;
 c) optionally crossing the selected F1 progeny or further selfing progeny with either parent, to produce backcross progeny;
 d) selecting backcross progeny which may comprise the desired trait and showing a broad spectrum resistance to *Bremia lactucae* or which comprises the said resistance allele; and
 e) optionally repeating steps c) and d) one or more times in succession to produce selected fourth or higher backcross progeny that may comprise the desired trait and a broad spectrum resistance to *Bremia lactucae*. The desired trait can be selected from, but not limited to, the following group: resistance to bacterial, fungal or viral diseases, insect or pest resistance, modified bolting, improved germination, plant size, plant type, improved shelf-life, water stress and heat stress tolerance, and male sterility. The invention includes a lettuce plant produced by this method.

In one embodiment, selection for plants showing a broad spectrum resistance to *Bremia lactucae* or which comprises the resistance allele is done in the F1 or any further generation by using markers CLS_S3_3349 (SEQ ID NO:1, SEQ ID NO:2) and/or CLS_S3_4656 (SEQ ID NO:3, SEQ ID NO:4). In another aspect, selection for the trait of the invention is started in the F2 of a cross or alternatively of a backcross. Selection of plants in the F2 can be done phenotypically as well as by using the said marker(s) which directly or indirectly detect(s) the resistance allele underlying the trait.

In one embodiment, selection for plants having a broad spectrum resistance to *Bremia lactucae* is started in the F3 or a later generation.

In one embodiment the plant which comprises the resistance allele is a plant of an inbred line, a hybrid, a doubled haploid, or of a segregating population.

The invention further provides a method for the production of a lettuce plant having a broad spectrum resistance to *Bremia lactucae* by using a doubled haploid generation technique to generate a doubled haploid line which comprises the said resistance.

The invention furthermore relates to hybrid seed that can be grown into a plant having a broad spectrum resistance to *Bremia lactucae* and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid lettuce plant having a broad spectrum resistance to *Bremia lactucae*, which may comprise crossing a first parent lettuce plant with a second parent lettuce plant, and harvesting the resultant hybrid seed, of which the first parent plant and/or the second parent plant have a broad spectrum resistance to *Bremia lactucae*, and growing said hybrid seeds into broad spectrum *Bremia lactucae* resistant hybrid plants.

The invention also relates to a method for the production of a lettuce plant having a broad spectrum resistance to *Bremia lactucae* by using a seed that comprises a resistance allele in its genome that leads to a broad spectrum resistance to *Bremia lactucae* for growing the said lettuce plant. The seeds are suitably seeds of cultivated lettuce plants which comprises a *Lactuca saligna* introgression on the bottom of linkage group 9, whereby said introgression fragment confers a broad spectrum *Bremia lactucae* resistance onto said cultivated lettuce plant, in particular seeds of which a representative sample was deposited under accession number NCIMB 42141.

The invention also relates to a method for seed production which may comprise growing lettuce plants from seeds of cultivated lettuce which may comprise a *Lactuca saligna* introgression on the bottom of linkage group 9, whereby said introgression fragment confers a broad spectrum *Bremia lactucae* resistance onto said cultivated lettuce plant, in particular seeds of which a representative sample was deposited under accession number NCIMB 42141, allowing the plants to produce seeds, and harvesting these seeds. Production of the seeds is suitably performed by crossing or selfing.

In one embodiment, the invention relates to a method for production of a lettuce plant having a broad spectrum resistance to *Bremia lactucae* by using tissue culture.

The invention further relates to a method for the production of a lettuce plant having a broad spectrum resistance to *Bremia lactucae* by using vegetative reproduction.

In one embodiment, the invention relates to a method for the production of a lettuce plant having a broad spectrum resistance to *Bremia lactucae* by using a method for genetic modification to introgress the said resistance phenotype and allele into the lettuce plant Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant Thus in one aspect of the invention, a transgenic lettuce plant is provided, which may comprise in its genome a plant promoter operably linked to a *Lactuca saligna* resistance allele of the invention, whereby the transgenic lettuce plant has a broad spectrum resistance to *Bremia lactucae*.

The invention also relates to a breeding method for the development of lettuce plants that have a broad spectrum resistance to *Bremia lactucae* wherein germplasm which comprises said resistance is used, such as any *Lactuca saligna* accession having broad spectrum resistance to *Bremia lactucae* which is conferred by a resistance allele located on the bottom of linkage group 9, or a cultivated lettuce plant which comprises such a *Lactuca saligna* introgression on linkage group 9 and otherwise a genome of *Lactuca sativa* (e.g. NCIMB 42141). Representative seed of said plant which comprises the resistance allele and being representative for the germplasm was deposited under accession number NCIMB 42141.

In a further embodiment, the invention relates to a method for the production of a lettuce plant having a broad spectrum resistance to *Bremia lactucae* wherein progeny or propagation material of a plant which comprises the resistance allele conferring said resistance is used as a source to introgress the said resistance into another lettuce plant Representative seed of said plant which comprises the resistance allele was deposited under accession number NCIMB 42141.

In one aspect, the invention provides a lettuce plant having a broad spectrum resistance to *Bremia lactucae*, which plant is obtainable by any of the methods herein described and/or familiar to the skilled person.

In one embodiment in the plants, seeds, progeny, propagation material, uses, nucleic acids and methods of the invention, the resistance allele is in one aspect of the invention the allele as present in the genome of plants grown from seeds of which a representative sample was deposited under accession number NCIMB 42141 and linked therein to markers CLS_S3_3349 (SEQ ID NO:1) and/or CLS_S3_4656 (SEQ ID NO:3).

"Lettuce" or "cultivated lettuce" or "cultivated *Lactuca sativa*" herein refers to plants of the species *Lactuca sativa* L. (or seeds from which the plants can be grown), and parts of such plants, bred by humans for food, and having agronomic characteristics. This includes any cultivated lettuce, such as breeding lines (e.g. backcross lines, inbred lines), cultivars, or varieties. Generally, heading and non-heading types of lettuce are distinguished. Heading types include for example, romaine (cos) types, crisphead, and butterhead types, while non-heading types include for example, leaf types. Cultivated lettuce plants are not "wild lettuce" plants or "wild *Lactuca*" plants, e.g. plants which generally have much poorer yields and poorer agronomic characteristics as compared to cultivated plants, and grow for example naturally in wild populations.

"Introgression from *Lactuca saligna*" or "introgression fragment from *Lactuca saligna*" herein refers to a fragment of a linkage group (or part of, or region of, a linkage group) which has been introduced from *Lactuca saligna* into cultivated lettuce (*Lactuca sativa*) by crossing or traditional breeding techniques, such as backcrossing e.g. the introgressed fragments is the result of breeding methods referred to by the verb "to introgress" (such as backcrossing). Such a cultivated lettuce plant thus has a "genome of cultivated *Lactuca sativa*", but may comprise in the genome a fragment of a wild lettuce e.g. an introgression fragment of a related wild *Lactuca* genome, such as *Lactuca saligna* e.g. the bott_C9 resistance allele, from CGN 15705 or other *Lactuca saligna* accessions, which confers broad spectrum *Bremia lactucae* resistance, as defined below. The introgression fragment may be large, e.g. even half of a chromosome, but is in particular smaller, such as 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as 200,000 bp (equals 200 kilo base pairs) or less, about 100,000 bp (equals 100 kb) or less, about 50,000 (50 kb) or less, about 25,000 (25 kb) or less. It is understood the term "introgression fragment" never includes the entire chromosome, but only part of the chromosome.

"Broad spectrum resistance" is to mean in the context of this application that the resistance conferred by the said resistance allele is to a number of, and optionally all officially recognized races or isolates of *Bremia lactucae* including, B1:1, and/or B1:2, and/or B1:4, and/or B1:5, and/or B1:6, and/or B1:7, and/or B1:10, and/or B1:12, and/or B1:13, and/or B1:14, and/or B1:15, and/or B1:16, and/or B1:17, and/or B1:18, and/or B1:20, and/or B1:21, and/or B1:22, and/or B1:23, and/or B1:24, and/or B1:25, and/or B1:26, and/or B1:27, and/or B1:28 (Van Ettekoven K and Van der Arend AJM (1999) Identification and denomination of "new" races of *Bremia lactucae*. In: Lebeda A, Kristkova E (eds.) Eucarpia leafy vegetables '99. Palacky University, Olomouc, Czech Republic: 171-175), and/or B1:29, and/or B1:30, and/or B1:31 (Plantum NL (Dutch association for breeding, tissue culture, production and trade of seeds and young plants), IBEB press release, "New races of *Bremia lactucae*, B1:29, B1:30 and B1:31 identified and nominated", August 2013), and/or Ca-I, and/or Ca-IIA, and/or Ca-IIB, and/or Ca-III, and/or CA-IV (Schettini et al. (1999) Insensitivity to metalaxyl in California populations of *Bremia lactucae* and resistance of California lettuce cultivars to downy mildew. Phytopathology, 81(1): 64-70), and/or Ca-V, and/or Ca-VI, and/or Ca-VII, and/or Ca-VIII (Michelmore and Ochoa (2006) Breeding crisphead lettuce. In: California Lettuce Research Board, Annual report 2005-2006. Salinas, Calif.: 55-68).

A lettuce plant having "broad spectrum resistance to *Bremia lactucae*" or "the *Bremia* resistance phenotype or trait" herein refers to a lettuce plant, variety, accession, line, etc. having an average percentage of sporulation of less than 10%, when tested in an Adult Plant Disease Test as described herein, against a number of, and in one aspect against all officially recognized races or isolates of *Bremia lactucae* including, Bl:1, and/or Bl:2, and/or Bl:4, and/or Bl:5, and/or Bl:6, and/or Bl:7, and/or Bl:10, and/or Bl:12, and/or Bl:13, and/or Bl:14, and/or Bl:15, and/or Bl:16, and/or Bl:17, and/or Bl:18, and/or Bl:20, and/or Bl:21, and/or Bl:22, and/or Bl:23, and/or Bl:24, and/or Bl:25, and/or Bl:26, and/or Bl:27, and/or Bl:28, and/or Bl:29, and/or Bl:30, and/or Bl:31 and/or Ca-I, and/or Ca-IIA, and/or Ca-IIB, and/or Ca-III, and/or CA-IV, and/or Ca-V, and/or Ca-VI, and/or Ca-VII, and/or Ca-VIII.

A lettuce plant having a "broad spectrum resistance to *Bremia lactucae*" or "the *Bremia* resistance phenotype or trait" herein further refers to a lettuce plant, variety, accession, line, etc. to lettuce plants having an average percentage of sporulation of less than 15% sporulation when tested in an Adult Plant Disease Test as described herein, against a number of, and in one aspect against all officially recognized races or isolates of *Bremia lactucae* as previously mentioned.

A lettuce plant having a "broad spectrum resistance to *Bremia lactucae*" or "the *Bremia* resistance phenotype or trait" herein further refers to a lettuce plant, variety, accession, line, etc. to lettuce plants having an average percentage of sporulation of less than 20% sporulation when tested in an Adult Plant Disease Test as described herein, against a number of, and in one aspect against all officially recognized races or isolates of *Bremia lactucae* as previously mentioned.

As used herein, a linkage group is a chromosome or a part of a chromosome, which is characterised by a range of genes and/or DNA-markers which are shown to be linked to one another, i.e. (1) to inherit together more frequently than may be expected on the basis of coincidence (genetically linked), and/or (2) to be positioned on the same DNA-strain (physically linked).

"Bottom of linkage group 9" or "bott_C9" or "bott_C9 resistance allele" or "bottom of C9" herein refers to the *Lactuca saligna* allele which confers broad spectrum resistance to *Bremia lactucae* (as defined below) and which is located on the lower or bottom portion of linkage group 9, below marker CLS_S3_7932, which is a marker also found on the integrated genetic map of lettuce (Truco et. al. (2007) Theoretical and Applied Genetics, 115(6): 735-46) (see also FIG. 2).

"Linked markers" herein refers to molecular markers and/or phenotypic markers that co-segregate with the *Bremia* resistance phenotype or trait, such that by following the inheritance of the said molecular markers and/or phenotypic markers the inheritance of the trait can be followed. "Markers linked" to the bott_C9 resistance allele are in one aspect located less than about 10 cM, such as less than about 9, 8, 7, 6, 5, 4, 3, 2, or 1 cM away from the bott_C9 resistance allele.

"Resistance" herein refers to the ability of a lettuce plant, variety, accession, line, etc. to restrict the growth and development of *Bremia lactucae* and/or the damage that is caused by said oomycete, as compared to the ability to do so of a susceptible lettuce plant, variety accession, or line under similar environmental conditions and disease pressure.

The "average percentage of sporulation" may be calculated as either the average of individual isolates across leaf discs and plants, or it may be the overall average across leaf discs, plants, and isolates (e.g. 2, 3, 4, 5, 6, 7, 8, 9, 10, or more, or all isolates).

"Physical distance" between loci (e.g. between molecular markers and/or between phenotypic markers) on the same chromosome is the actual physical distance expressed in base pairs (bp), kilo base pairs (kb), or mega base pairs (Mb).

Genetic distance" between loci (e.g. between molecular markers and/or between phenoptypic markers) on the same linkage group is measured by frequency of crossing-over, or recombination frequency (RF), and is indicated in centimorgans (cM). One cM corresponds to a recombination frequency of 1%. If no recombinants can be found, the RF is zero and the loci are either extremely close together physically, or they are identical. The further apart two loci are, the higher the RF.

The term "resistance allele" as used herein encompasses one or more QTLs, genes, or tightly linked alleles located on the bottom of linkage group 9, which confer broad spectrum resistance to *Bremia lactucae*. These terms are used interchangeably. A resistance allele can alternatively be identified by the position on a genetic map, or by indication of the location on a linkage group or chromosome. When a resistance allele is no longer linked to a specific molecular marker, but its position on a chromosome as defined on a genetic map is unaltered, this resistance allele is still the same as when it was linked to the molecular marker. The genetic trait that it confers is therefore also still the same.

The word "trait" in the context of this application refers to the phenotype of the plant. In particular, the word "trait" refers to the trait of the invention, more in particular to a broad spectrum resistance to *Bremia lactucae*.

The term "progeny" or "descendant" used herein is intended to mean the first (F1) and all subsequent descendants (e.g. further selfing and/or crossing and/or backcross progeny) from a cross with a plant of the invention that comprises said broad spectrum resistance conferred by the introgression fragment (which comprises the resistance allele) on the bottom of linkage group 9. "Progeny" or "descendants" also encompasses plants that carry the trait of the invention (the broad spectrum resistance conferred by the introgression on the bottom of linkage group 9) and are obtained from other plants or progeny of plants of the invention by vegetative propagation or multiplication.

Representative seeds of *Lactuca sativa* containing the resistance allele of the invention which confers broad spectrum resistance to *Bremia lactucae* were deposited by Rijk Zwaan Zaadteelt en Zaadhandel B. V. (Burgemeester Crezeelaan 40, 2678 KX, De Lier, The Netherlands) under accession number NCIMB 42141 on 18 Apr. 2013 with NCIMB Ltd. (Ferguson Building, Craibstone Estate, Bucksburn, Aberdeen, AB21 9YA).

All seeds of the deposit comprises the resistance allele homozygously. At the time of filing, plants grown from these seeds are thus resistant against a number of, and optionally all officially recognized races or isolates of *Bremia lactucae* including, Bl:1, and/or Bl:2, and/or Bl:4, and/or Bl:5, and/or Bl:6, and/or Bl:7, and/or Bl:10, and/or Bl:12, and/or Bl:13, and/or Bl:14, and/or Bl:15, and/or Bl:16, and/or Bl:17, and/or Bl:18, and/or Bl:20, and/or Bl:21, and/or Bl:22, and/or Bl:23, and/or Bl:24, and/or Bl:25, and/or Bl:26, and/or Bl:27, and/or Bl:28, and/or Bl:29, and/or Bl:30, and/or Bl:31, and/or Ca-I, and/or Ca-IIA, and/or Ca-IIB, and/or Ca-III, and/or CA-IV, and/or Ca-V, and/or Ca-VI, and/or Ca-VII, and/or Ca-VIII.

The deposited seeds do not meet the DUS criteria which are required for obtaining plant variety protection, and can therefore not be considered to be a plant variety.

TABLE 1

Sequence data of the DNA markers
In the deposit NCIMB 42141, the markers CLS_S3_3349 and/or CLS_S3_4656 are linked to the resistance allele conferring broad spectrum resistance to Bremia lactucae. Differences in nucleotide sequence between the (*L. saligna*) resistant and (*L. sativa*) susceptible alleles for each marker, are indicated in between square brackets [].

| Marker Name | Sequence | Amplification Primers |
|---|---|---|
| CLS_S3_3349<br>(resistant allele)<br>(SEQ ID NO: 1) | TTATTCTGCTGCCAACAAGAA[C]<br>ATGGCTGTGACCTGGGGAGAG<br>AATACACTCTATGACTACTT[G]<br>CTAAACCCTAAGAAGGTACAAG<br>AC[C]ACATATATCATTTGAAAC<br>TTGA[G]AGGTCCTAATTCACAT<br>CACA[TTTTCTT]TTTTCTTTTTTC<br>TTTTTTCTTATAAATTGTGAAAC<br>TCATGTTG | Forward:<br>CTTTTTGGAAGGCAATCTGG<br>(SEQ ID NO: 6)<br>Reverse:<br>TCCAGGGAAAACCATCTTTG<br>(SEQ ID NO: 7) |
| CLS_S3_3349<br>(susceptible<br>allele)<br>(SEQ ID NO: 2) | TTATTCTGCTGCCAACAAGAA[T]<br>ATGGCTGTGACCTGGGGAGAG<br>AATACACTCTATGACTACTT[A]<br>CTAAACCCTAAGAAGGTACAAG<br>AC[T]ACATATATCATTTGAAAC<br>TTGA[A]AGGTCCTAATTCACAT<br>CACA[-]<br>TTTTCTTTTTTCTTTTTTCTTATA<br>AATTGTGAAACTCATGTTG | Forward:<br>CTTTTTGGAAGGCAATCTGG<br>(SEQ ID NO: 6)<br>Reverse:<br>TCCAGGGAAAACCATCTTTG<br>(SEQ ID NO: 7) |
| CLS_S3_4656<br>(resistant allele)<br>(SEQ ID NO: 3) | TTTTTTTTTGGTAAACAGCATA<br>[TCTCCAG]TCTCCTTGATCCTTCT<br>TTCTCTCCTGCAACCATAAGAC<br>ATGTATC[T]GTTTAAGATTTAGC<br>CTTGGTTTCTAACTTTATGATCA<br>GTGCCCTTTCAACTTT[-]<br>CTTCTT[C]AAGTAAGATGAGTT<br>ACCCCT[T]AATCCTAA[C]TCAA<br>ATTCCCCCAATATTCTT[G]TTCA<br>ATTA | Forward:<br>CCGTATGCCGTTCATCTTCT<br>(SEQ ID NO: 8)<br>Reverse:<br>GCACTCCAATTGAATGATCG<br>(SEQ ID NO: 9) |
| CLS_S3_4656<br>(susceptible<br>allele)<br>(SEQ ID NO: 4) | TTTTTTTTTGGTAAACAGCATA[-<br>TCTCCTTGATCCTTCTTTCTCTC<br>CTGCAACCATAAGACATGTATC<br>[G]GTTTAAGATTTAGCCTTGGTT<br>TCTAACTTTATGATCAGTGCCCT<br>TTCAACTTT[T]CTTCTT[T]AAGT<br>AAGATGAGTTACCCCT[A]AATC<br>CTAA[T]TCAAATTCCCCCAATAT<br>TCTT[A]TTCAATTA | Forward<br>CCGTATGCCGTTCATCTTCT<br>SEQ ID NO: 8)<br>Reverse:<br>GCACTCCAATTGAATGATCG<br>(SEQ ID NO: 9) |
| CLS_S3_7932<br>(SEQ ID NO: 5) | CTTCTTCTACAACATGATTTCGG<br>ATACACTTACGGCAGTCCACCA<br>GTCTCCGCCCAATACACCCCGC<br>CGTCGAATTGCCCATCAACCGA<br>TTTTGCGAAAATTGTTCTCGAAT<br>GGACAGCTACATGT | Forward:<br>ACACAAAACCCTGCTCAACC<br>Reverse:<br>CGATCGAATTGACGACCTTT |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1A: Young Plant Disease Test

A young plant disease test (YDT) was performed on 2-3 week old plants (e.g. 1 to 3 expanded leaves). Vital plants (e.g. plants not malformed, stunted, bleached or necrotic), were inoculated with each *Bremia lactucae* strain to be tested at a spore concentration of approximately $10^4$-$10^5$ spores/ml. Plants were grown in a climate chamber with a photoperiod of 16 h, light intensity of approximately 250 μmol $m^{-2}$ $s^{-1}$, relative humidity (RH) of 70%, and a constant temperature of 15° C.

Following inoculation, plants were placed in a transparent plastic cage to maintain 100% RH. Plants were categorized for absence or presence of infection, based on observations from 8 to 14 days post inoculation (dpi). The level of infection was scored at 8 dpi and 9 dpi based upon the most infected leaf, in terms of percentage of leaf area covered with sporulation (e.g. 0% to 100% sporulation). Scoring was performed by a single person in order to prevent scoring biases.

Example 1B: Adult Plant Disease Test

A leaf disc test was employed for *Bremia lactucae* adult plant disease testing on leaf discs of 8 week old plants (e.g. 6-8 leaf stage), before the plants have started to bolt. This was done to ensure that bolting did not have an influence on resistance scoring. For each *Bremia lactucae* strain to be tested, 3 or 4 leaf discs per plant were sampled, such that each of the leaf discs were sampled from different leaves of the plant.

Leaf discs of 17 millimeter in diameter were used for testing. The leaf discs were placed upside down on filter paper moistened with water in a plastic box. Leaf discs were then inoculated by spraying with a spore suspension of the *Bremia lactucae* strain to be tested, at a spore concentration of approximately $10^4$-$10^5$ spores per ml. Leaf discs of resistant and susceptible controls were also included in the test.

Directly following inoculation, the leaf discs were placed in a climate cell and incubated in the dark for at least 12 hours. The filter paper was kept moistened with water to ensure that the humidity in the box remained at 95-100% humidity. Subsequently, the plastic boxes containing the leaf discs were then transferred to a climate cell with the following growth conditions: photoactive period of 12 hours, constant temperature of 15° C., and light conditions of 20 W/m².

Figure 1:
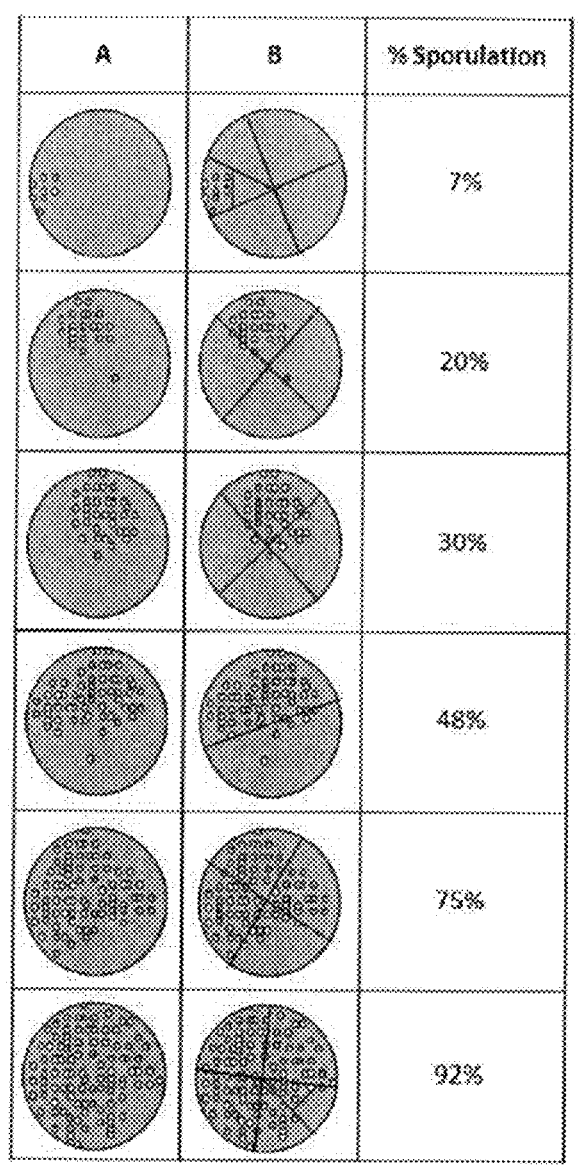
FIG. 1: Determining the percentage of sporulation on a leaf disc surface infected with *Bremia lactucae*. The illustration shown can be used as a guideline for estimating the percentage of sporulation on a leaf disc.

The leaf discs were scored at 8, 10 and 13 days post-inoculation for infection severity levels. Each leaf disc was scored based upon the percentage of sporulation on the leaf disc surface (e.g. 0% to 100% sporulation) (FIG. 1). Scoring was performed by a single person in order to prevent scoring biases.

Example 2: Identification of the Resistance Allele on Linkage Group 9

*Lactuca saligna* CGN 15705 was found according to the invention to have a broad spectrum resistance to *Bremia lactucae*.

An initial crossing was made between plants of *Lactuca saligna* CGN 15705, and *Lactuca sativa* cv. Olof. Resulting F1 plants were backcrossed to the recurrent *Lactuca sativa* parent and/or selfed to generate BC1 sativa and F2 segregating populations, respectively.

Disease testing for *Bremia* resistance was performed on these two populations using various *Bremia lactucae* isolates, for example B1:16, B1:21, and B1:24, following the testing methods as described in EXAMPLE 1A and/or 1B. Additionally, *L. saligna* CGN 15705, *L. sativa* cv. Olof, and *L. sativa* cv. Cobham Green (susceptible line) were included as controls in the disease test.

562 F2 seeds were shown from a single F1 plant, and of these, 509 F2 seeds germinated. F2 plants that were highly susceptible or highly resistant to *Bremia lactucae* isolate B1:21, and that were vital, at a young plant stage as described in EXAMPLE 1A were selected for further testing. Adult plant disease testing as described in EXAMPLE 1B was then performed using *Bremia lactucae* isolates B1:16 and B1:21 on the selected F2 plants from the young disease test. Following adult plant disease testing, 40 F2 plants remained in the highly resistant group, while 16 F2 plants remained in the highly susceptible group. Collectively, these 56 F2 plants were used for QTL mapping.

63 plants of the BC1 sativa population that were not malformed, stunted, bleached or necrotic, were tested using the adult plant disease testing method as described in EXAMPLE 1B using *Bremia lactucae* isolates B1:21 and B1:24, and used for QTL mapping.

QTL mapping using the Kruskal-Wallis test (alpha=0.005, MapQTL 4.1, Kyazma B. V., Wageningen, The Netherlands) and genotype segregation analysis was performed on the BC1 sativa and selected F2 population, using 85 markers that were evenly distributed over the 9 linkage groups. The skilled person is familiar with performing such a QTL mapping analysis (Van Ooijen (2004). MapQTL® 5, Software for the mapping of quantitative trait loci in experimental populations. Kyazma B. V., Wageningen, The Netherlands).

A resistance allele located at the bottom of linkage group 9, herein referred to as bott_C9, was identified. Bott_C9 showed a high association with resistance against several *Bremia lactucae* isolates, for example B1:16, B1:21 and B1:24, in the BC1sativa and F2 populations. Moreover, the bott_C9 resistance allele can be identified by markers CLS_S3_3349 (SEQ ID NO:1), and/or CLS_S3_4656 (SEQ ID NO:3), and/or other linked markers which are less than 10 cM away from the resistance allele (FIG. 2).

Example 3: Verification of the Bott_C9 Resistance Allele

The BC1sativaS1 population was used to verify the bott_C9 resistance allele of EXAMPLE 2. Markers closely linked to bott_C9, CLS_S3_3349 (SEQ ID NO:1, SEQ ID NO:2) and CLS_S3_4656 (SEQ ID NO:3, SEQ ID NO:4), were used to genotype individual plants of this population.

The BC1sativaS1 population consisted of 17 plants resulting from self-fertilization of a single plant from the BC1sativa population of EXAMPLE 2. The BC1sativa parent plant was heterozygous at bott_C9. Markers CLS_S3_3349 (SEQ ID NO:1, SEQ ID NO:2) and CLS_S3_4656 (SEQ ID NO:3, SEQ ID NO:4) were used to genotype the BC1sativaS1 population as follows: 4 BC1sativaS1 plants were heterozygous at bott_C9, and 13 BC1sativaS1 were homozygous for the *L. sativa* allele at bott_C9.

*Bremia* disease testing was also performed on individual plants of the BC1sativaS1 population, as described in EXAMPLE 1B, using various *Bremia lactucae* isolates, for example B1:10, B1:15, B1:21, B1:25, B1:26, B1:27 and B1:28. The genotypes and disease scores are summarized in Table 2. The results indicate that the *L. saligna* bott_C9 resistance allele provides broad spectrum resistance to *Bremia lactucae*.

Logit-transformed sporulation percentages were statistically analyzed by a linear mixed model with plants, leaves and test boxes as random effects. There was no significant isolate x bott_C9 genotype effect (P>0.1), which confirms the broad spectrum resistance to *Bremia lactucae* provided by the *L. saligna* allele at bott_C9. Additionally the results demonstrate that the high level of resistance seen in the heterozygous plants indicate that the *L. saligna* allele at bott_C9 is dominant over the *L. sativa* allele. Collectively, the results confirm that the bott_C9 resistance allele from *L. saligna*, which is located on linkage group 9 and linked to markers CLS_S3_3349 (SEQ ID NO:1) and/or CLS_S3_4656 (SEQ ID NO:3), provides a broad spectrum resistance to *Bremia lactucae*.

TABLE 2

Percentage of sporulation at 8, 10, and 13 days post inoculation. Scores are averaged across leaf discs, plants, Bremia isolates and spore concentrations.

| Genotype | Bott_C9 Genotype | Sporulation (%) on leaf discs | | | Mean sporulation | Status |
|---|---|---|---|---|---|---|
| | | 8 DPI | 10 DPI | 13 DPI | (%)across DPI | |
| L. sativa cv. Cobham Green | A | 18 | 41 | 72 | 43.6 | Susceptible |
| L. sativa cv. Olof | A | 13 | 39 | 73 | 41.5 | Susceptible |
| L. satigna CGN15705 | B | 0 | 0 | 0 | 0.1 | Broad spectrum resistance |
| BC1sativaS1 (n = 13) | A | 9 | 24 | 43 | 25.1 | Susceptible |
| BC1sativaS1 (n = 4) | H | 1 | 4 | 7 | 4.2 | Broad spectrum resistance |

A = homozygous L. sativa at bott_C9, H = heterozygous, B = homozygous L. saligna at bott_C9, DPI = days post inoculation.

Example 4: Transfer of the Bott_C9 Resistance Allele to Susceptible Lettuce Plants From the F2 population of EXAMPLE 2, an F2 plant homozygous for the L. saligna allele at bott_C9 and found to have a broad spectrum resistance to Bremia lactucae, was selfed to produce F3 seed, representative seeds of which were deposited with the NCIMB under accession number NCIMB 42141.

A lettuce plant of the invention grown from a seed of which a representative sample was deposited under accession number NCIMB 42141, and which had a broad spectrum resistance to Bremia lactucae, was crossed with an L. sativa cv. Sensaï plant susceptible to Bremia isolate B1:28.

From the F1 population, which was grown from F1 seeds, a plant was selected which was selfed to obtain a population of F2 plants. The F2 plants were tested using the adult plant disease test as described in EXAMPLE 1B, using Bremia lactucae isolate B1:28. The segregation of the F2 population for B1:28 resistance demonstrated that the resistance of the invention was consistent with that of a monogenic dominant trait. Resistant F2 plants were selected and genotyped using closely linked markers CLS_S3_3349 (SEQ ID NO:1, SEQ ID NO:2) and CLS_S3_4656 (SEQ ID NO:3, SEQ ID NO:4), to select for plants homozygous for the L. saligna bott_C9 allele.

F2 plants homozygous for the L. saligna bott_C9 allele were then selfed to obtain a population of F3 plants. The F3 plants were tested using the adult plant disease test as described in Example 1B, using Bremia lactucae isolate B1:28. All F3 plants tested were resistant against B1:28. Additional testing with other Bremia isolates, for example B1:20, B1:22, B1:24, B1:25, B1:26 and B1:27, confirmed the Bremia lactucae broad spectrum resistance of the invention.

Since the F3 population showed no segregation of the resistance of the invention, this demonstrates that the F3 seed was in fact homozygous and uniform for the L. saligna bott_C9 allele, which confers broad spectrum resistance to Bremia lactucae.

The invention is further described by the following numbered paragraphs:

1. A lettuce plant (Lactuca sativa L.) comprising a resistance allele from L. saligna which confers a broad spectrum resistance to Bremia lactucae, wherein the resistance allele is located on the bottom of linkage group 9.
2. A lettuce plant according to paragraph 1, wherein the resistance allele is as found in the genome of plants grown from seeds of which a representative sample was deposited under accession number NCIMB 42141.
3. A lettuce plant (Lactuca sativa L.) according to paragraph 1 and/or 2, wherein the plant comprises in its genome at least one marker selected from the group: marker CLS_S3_3349 (SEQ ID NO:1), marker CLS_S3_4656 (SEQ ID NO:3), any L. saligna-genome specific marker in between marker CLS_S3_3349 and marker CLS_S3_4656.
4. Seed capable of growing into a lettuce plant of any one of paragraphs 1 to 3.
5. Seed produced on a lettuce plant of any one of paragraphs 1 to 3, wherein the lettuce plant that can be grown from the seed has a broad spectrum resistance to Bremia lactucae as defined in any one of paragraphs 1 to 3.
6. Progeny of a lettuce plant as defined in any one of paragraphs 1 to 3, wherein the progeny plant has a broad spectrum resistance to Bremia lactucae as defined in any one of paragraphs 1 to 3.
7. Propagation material derived from a plant of any one of paragraphs 1 to 3, wherein the propagation material comprises the resistance allele as defined in any one of paragraphs 1 to 3.
8. Propagation material of paragraph 7, capable of growing into a plant of any one of paragraphs 1 to 3.
9. Propagation material of paragraphs 7 or 8, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.
10. Tissue culture of propagation material of any of paragraphs 7 to 9.
11. Part of a lettuce plant of any one of paragraphs 1 to 3, and 6, which part is in particular a harvested lettuce head and/or leaf, and is optionally in processed form.
12. Part of a lettuce plant of paragraph 11, wherein the part is a food product or part thereof.
13. A nucleic acid molecule causative of a broad spectrum resistance to Bremia lactucae, comprising a DNA sequence, which is linked to markers CLS_S3_3349 (SEQ ID NO:1) and/or CLS_S3_4656 (SEQ ID NO:3) located on linkage group 9, or a resistance conferring part of said nucleic acid molecule.
14. The nucleic acid molecule of paragraph 13, comprising the resistance allele as defined in any one of paragraphs 1 to 3, which allele is optionally linked to markers CLS_S3_3349 (SEQ ID NO:1) and/or CLS_S3_4656 (SEQ ID NO:3).
15. Use of the markers as defined in paragraph 3, to identify or develop broad spectrum Bremia lactucae resistant plants, or develop other markers linked to the resistance allele as defined in any one of paragraphs 1 to 3.
16. Use of a plant of any one of paragraphs 1 to 3 and 6, or plants produced from the seed of paragraph 4 or 5, as germplasm in a breeding program for the development of *Lactuca sativa* plants having a broad spectrum resistance to *Bremia lactucae*.

17. A method for producing a cultivated lettuce plant having a broad spectrum resistance to *Bremia lactucae*, comprising:
    a) crossing a *L. saligna* or *L. sativa* plant comprising a resistance allele that leads to a broad spectrum resistance to *Bremia lactucae* with a lettuce plant;
    b) optionally selfing the resulting F1 one or more times for obtaining F2, F3 or further selfing progeny plants;
    c) selecting plants having a broad spectrum resistance to *Bremia lactucae*;
    d) optionally performing one or more additional rounds of selfing and/or crossing, and subsequently selecting for a plant comprising broad spectrum resistance to *Bremia lactucae*, wherein the resistance allele is located on the bottom of linkage group 9.

18. A method for producing a cultivated lettuce plant having a broad spectrum resistance to *Bremia lactucae*, comprising:
    a) crossing a *L. saligna* or *L. sativa* plant comprising a resistance allele that leads to a broad spectrum resistance to *Bremia lactucae* with another lettuce plant;
    b) optionally selfing the F1 one or more times to produce an F2, F3, or further selfing progeny;
    c) optionally backcrossing the resulting F1 or F2, F3, or further selfing progeny with either parent to obtain a backcross progeny plant;
    d) selecting for plants that have a broad spectrum resistance to *Bremia lactucae* in the F1, F2, F3 or further selfing progeny or backcross progeny;
    e) optionally performing one or more additional rounds of selfing or crossing, and subsequently selecting for a plant showing said broad spectrum resistance to *Bremia lactucae* and comprising said resistance allele, wherein the resistance allele is located on the bottom of linkage group 9.

19. The method of paragraph 17 or 18, wherein the plant comprising a resistance allele is a plant as defined in any one of paragraphs 1-3.

20. A method for seed production comprising growing lettuce plants from seeds of cultivated lettuce of paragraph 4, allowing the plants to produce seeds, and harvesting these seeds.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A *Lactuca sativa* L. plant comprising a resistance allele from *L. saligna* which confers a broad spectrum resistance to *Bremia lactucae* when the resistance allele is in heterozygous or homozygous form, wherein the resistance allele is located on linkage group 9 and comprises marker CLS_S3_3349 and/or marker CLS_S3_4656, wherein broad-spectrum resistance is resistance to at least the following races or isolates of *Bremia lactucae*: Bl:10, Bl:15, Bl:16, Bl:20, Bl:21, Bl:22, Bl:24, Bl:25 Bl:26 Bl:27, and Bl:28 and wherein a representative sample of seed comprising the resistance allele was deposited under accession number NCIMB 42141.

2. The lettuce plant of claim 1, wherein the plant comprises in its genome marker CLS_S3_3349 (SEQ ID NO:1) and marker CLS_S3_4656 (SEQ ID NO:3).

3. A seed capable of growing into the lettuce plant of claim 1.

4. A seed produced on the lettuce plant of claim 1, wherein the lettuce plant that can be grown from the seed has the broad spectrum resistance to *Bremia lactucae*.

5. A progeny of the lettuce plant of claim 1, wherein the progeny plant has the broad spectrum resistance to *Bremia lactucae*.

6. A propagation material derived from the plant of claim 1, wherein the propagation material comprises the resistance allele.

7. The propagation material of claim 6, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast or cell.

8. A tissue culture of the propagation material of claim 6.

9. A part of the lettuce plant of claim 1, wherein the part is a harvested lettuce head or leaf, and wherein the part is optionally in processed form.

10. A food product or part thereof, comprising the part of the lettuce plant of claim 9.

11. A method of developing *Lactuca sativa* plants having a broad spectrum resistance to *Bremia lactucae*, said method comprising isolating germplasm from the plant of claim 1 for a breeding program.

12. A method for seed production, said method comprising growing a lettuce plant from the seed of claim 3, allowing the plants to produce seeds, and harvesting the seeds.

* * * * *

SEQUENCE LISTING

```
<160> NUMBER OF SEQ ID NOS: 11

<210> SEQ ID NO 1
<211> LENGTH: 182
<212> TYPE: DNA
<213> ORGANISM: Lactuca sativa
<220> FEATURE:
<221> NAME/KEY: source
<222> LOCATION: 1..182
<223> OTHER INFORMATION: /organism="Lactuca sativa"
      /mol_type="unassigned DNA"

<400> SEQUENCE: 1
ttattctgct gccaacaaga acatggctgt gacctgggga gagaatacac tctatgacta      60
cttgctaaac cctaagaagg tacaagacca catatatcat ttgaaacttg agaggtccta     120
attcacatca cattttcttt tttctttttt cttttttctt ataaattgtg aaactcatgt     180
tg                                                                    182

<210> SEQ ID NO 2
<211> LENGTH: 175
<212> TYPE: DNA
<213> ORGANISM: Lactuca sativa
<220> FEATURE:
<221> NAME/KEY: source
<222> LOCATION: 1..175
<223> OTHER INFORMATION: /organism="Lactuca sativa"
      /mol_type="unassigned DNA"

<400> SEQUENCE: 2
ttattctgct gccaacaaga atatggctgt gacctgggga gagaatacac tctatgacta      60
cttactaaac cctaagaagg tacaagacta catatatcat ttgaacttg aaaggtccta     120 attcacatca cattttcttt tttctttttt cttataaatt gtgaaactca tgttg           175

<210> SEQ ID NO 3
<211> LENGTH: 195
```

```
<212> TYPE: DNA
<213> ORGANISM: Lactuca sativa
<220> FEATURE:
<221> NAME/KEY: source
<222> LOCATION: 1..195
<223> OTHER INFORMATION: /organism="Lactuca sativa"
      /mol_type="unassigned DNA"

<400> SEQUENCE: 3 ttttttttg gtaaacagca tatctccagt ctccttgatc cttctttctc tcctgcaacc      60
ataagacatg tatctgttta agatttagcc ttggtttcta actttatgat cagtgccctt    120
tcaactttct tcttcaagta agatgagtta ccccttaatc ctaactcaaa ttcccccaat    180
attcttgttc aatta                                                    195

<210> SEQ ID NO 4
<211> LENGTH: 189
<212> TYPE: DNA
<213> ORGANISM: Lactuca sativa
<220> FEATURE:
<221> NAME/KEY: source
<222> LOCATION: 1..189
<223> OTHER INFORMATION: /organism="Lactuca sativa"
      /mol_type="unassigned DNA"

<400> SEQUENCE: 4 ttttttttg gtaaacagca tatctccttg atccttcttt ctctcctgca accataagac      60
atgtatcggt ttaagattta gccttggttt ctaactttat gatcagtgcc ctttcaactt    120
ttcttcttta agtaagatga gttaccccta atcctaatt caaattcccc caatattctt    180
attcaatta                                                           189

<210> SEQ ID NO 5
<211> LENGTH: 126
<212> TYPE: DNA
<213> ORGANISM: Lactuca sativa
<220> FEATURE:
<221> NAME/KEY: source
<222> LOCATION: 1..126
<223> OTHER INFORMATION: /organism="Lactuca sativa"
      /mol_type="unassigned DNA"

<400> SEQUENCE: 5
cttcttctac aacatgattt cggatacact tacggcagtc caccagtctc cgcccaatac      60
accccgccgt cgaattgccc atcaaccgat tttgcgaaaa ttgttctcga atggacagct    120
acatgt                                                              126

<210> SEQ ID NO 6
<211> LENGTH: 20
<212> TYPE: DNA
<213> ORGANISM: Lactuca sativa
<220> FEATURE:
<221> NAME/KEY: source
<222> LOCATION: 1..20
<223> OTHER INFORMATION: /organism="Lactuca sativa"
      /mol_type="unassigned DNA"

<400> SEQUENCE: 6 cttttttggaa ggcaatctgg                                               20

<210> SEQ ID NO 7
<211> LENGTH: 20
<212> TYPE: DNA
<213> ORGANISM: Lactuca sativa
<220> FEATURE:
```

```
<221> NAME/KEY: source
<222> LOCATION: 1..20
<223> OTHER INFORMATION: /organism="Lactuca sativa"
      /mol_type="unassigned DNA"

<400> SEQUENCE: 7
tccagggaaa accatctttg                                               20

<210> SEQ ID NO 8
<211> LENGTH: 20
<212> TYPE: DNA
<213> ORGANISM: Lactuca sativa
<220> FEATURE:
<221> NAME/KEY: source
<222> LOCATION: 1..20
<223> OTHER INFORMATION: /organism="Lactuca sativa"
      /mol_type="unassigned DNA"

<400> SEQUENCE: 8
ccgtatgccg ttcatcttct                                               20

<210> SEQ ID NO 9
<211> LENGTH: 20
<212> TYPE: DNA
<213> ORGANISM: Lactuca sativa
<220> FEATURE:
<221> NAME/KEY: source
<222> LOCATION: 1..20
<223> OTHER INFORMATION: /organism="Lactuca sativa"
      /mol_type="unassigned DNA"

<400> SEQUENCE: 9
gcactccaat tgaatgatcg                                               20

<210> SEQ ID NO 10
<211> LENGTH: 20
<212> TYPE: DNA
<213> ORGANISM: Lactuca sativa
<220> FEATURE:
<221> NAME/KEY: source
<222> LOCATION: 1..20
<223> OTHER INFORMATION: /organism="Lactuca sativa"
      /mol_type="unassigned DNA"

<400> SEQUENCE: 10
acacaaaacc ctgctcaacc                                               20

<210> SEQ ID NO 11
<211> LENGTH: 20
<212> TYPE: DNA
<213> ORGANISM: Lactuca sativa
<220> FEATURE:
<221> NAME/KEY: source
<222> LOCATION: 1..20
<223> OTHER INFORMATION: /organism="Lactuca sativa"
      /mol_type="unassigned DNA"

<400> SEQUENCE: 11
cgatcgaatt gacgaccttt                                               20
```